(12) United States Patent
Shiraki et al.

(10) Patent No.: US 9,394,213 B2
(45) Date of Patent: Jul. 19, 2016

(54) METHOD FOR PRODUCING α-OLEFIN

(71) Applicant: IDEMITSU KOSAN CO., LTD., Chiyoda-ku (JP)

(72) Inventors: Yasushi Shiraki, Ichihara (JP); Masahiko Kuramoto, Ichihara (JP); Takuji Okamoto, Ichihara (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 210 days.

(21) Appl. No.: 14/369,509

(22) PCT Filed: Dec. 13, 2012

(86) PCT No.: PCT/JP2012/082359
§ 371 (c)(1),
(2) Date: Jun. 27, 2014

(87) PCT Pub. No.: WO2013/099626
PCT Pub. Date: Jul. 4, 2013

(65) Prior Publication Data
US 2014/0364669 A1 Dec. 11, 2014

(30) Foreign Application Priority Data
Dec. 27, 2011 (JP) ................................. 2011-286983

(51) Int. Cl.
| | | |
|---|---|---|
| *C08F 4/06* | (2006.01) | |
| *C08F 4/24* | (2006.01) | |
| *C08F 4/00* | (2006.01) | |
| *C08F 2/00* | (2006.01) | |
| *C08F 210/00* | (2006.01) | |
| *C07C 2/26* | (2006.01) | |
| *C07C 2/34* | (2006.01) | |
| *C07C 2/32* | (2006.01) | |
| *B01J 31/14* | (2006.01) | |
| *B01J 31/18* | (2006.01) | |

(52) U.S. Cl.
CPC ................ *C07C 2/34* (2013.01); *B01J 31/143* (2013.01); *B01J 31/146* (2013.01); *B01J 31/188* (2013.01); *C07C 2/32* (2013.01); *B01J 2531/007* (2013.01); *B01J 2531/62* (2013.01); *C07C 2531/12* (2013.01); *C07C 2531/14* (2013.01); *C07C 2531/24* (2013.01); *C07C 2531/34* (2013.01)

(58) Field of Classification Search
CPC ............ C07C 3/32; C07C 2/34; C07C 11/02; C07C 2531/24; C07C 2531/34; C07C 2531/12; C07C 2531/14; B01J 31/143; B01J 31/146; B01J 31/188; B01J 2531/007; B01J 2531/62
USPC ............ 525/511; 585/99, 100, 104, 193, 236, 585/348
See application file for complete search history.

(56) References Cited

U.S. PATENT DOCUMENTS

| | | |
|---|---|---|
| 7,525,009 B2 | 4/2009 | Blann et al. |
| 2005/0119516 A1 | 6/2005 | Dixon et al. |
| 2005/0131262 A1 | 6/2005 | Dixon et al. |
| 2006/0128910 A1 | 6/2006 | Blann et al. |
| 2006/0173226 A1 | 8/2006 | Blann et al. |
| 2006/0229480 A1 | 10/2006 | Blann et al. |
| 2007/0232481 A1 | 10/2007 | Zhang et al. |
| 2008/0200744 A1 | 8/2008 | Dixon et al. |
| 2010/0190939 A1 | 7/2010 | Fritz et al. |

FOREIGN PATENT DOCUMENTS

| | | |
|---|---|---|
| JP | 6 329562 | 11/1994 |
| JP | 7 215896 | 8/1995 |
| JP | 8 183746 | 7/1996 |
| JP | 2002 532249 | 10/2002 |
| JP | 2003-261588 | * 9/2003 |
| JP | 2003 261588 | 9/2003 |
| JP | 2004 67511 | 3/2004 |
| JP | 2005 513115 | 5/2005 |
| JP | 2006 511694 | 4/2006 |
| JP | 2010 532711 | 10/2010 |

OTHER PUBLICATIONS

Annette Bollmann, et al., "Ethylene tetramerization: A new route to produce 1-Octene in exceptionally high selectivities", J. Am. Chem. Soc., vol. 126, 2004, pp. 14712-14713.
Matthew J. Overett, et al., "Carbon-bridged diphosphine ligands for chromium-catalysed ethylene tetramerisation and trimerisation reactions", Journal of Molecular Catalysis A: Chemical, vol. 283, 2008, pp. 114-119.
International Search Report Issued Mar. 12, 2013 in PCT/JP12/082359 Filed Dec. 13, 2012.

* cited by examiner

*Primary Examiner* — William Cheung
(74) *Attorney, Agent, or Firm* — Oblon, McClelland, Maier & Neustadt, L.L.P.

(57) ABSTRACT

Provided is a production process for α-olefin which does not comply the Shultz-Flory distribution and which is excellent in the yields of α-olefins of 1-hexene up to 1-tetradecene each having 6 to 14 carbon atoms, particularly a yield of 1-octene. The above production process is characterized by polymerizing ethylene using (A) a specific chromium compound, (B) a specific aminophosphine ligand compound and (C) a promoter.

14 Claims, No Drawings

METHOD FOR PRODUCING α-OLEFIN

CROSS REFERENCE TO RELATED APPLICATIONS

The present application is a 35 U.S.C. §371 national stage patent application of International patent application PCT/JP2012/082359, filed on Dec. 13, 2012, published as WO/2013/099626 on Jul. 4, 2013, the text of which is incorporated by reference, and claims the benefit of the filing date of Japanese application no. 2011-286983, filed on Dec. 27, 2011, the text of which is also incorporated by reference.

TECHNICAL FIELD

The present invention relates to a production process for α-olefins which are widely used on an industrial scale as comonomers of polyethylene and raw materials for synthetic lubricants, surfactants and the like.

BACKGROUND ART

In recent years, α-olefins, particularly 1-hexene, 1-octene and the like are widely used as comonomers of linear low density polyethylene (L-LDPE), and α-olefins up to 1-tetradecene having 14 carbon atoms including the above α-olefins are widely used in an application of synthetic lubricants and as raw materials for surfactants. Usually, the above α-olefins are obtained by polymerizing ethylene, and a polymerization degree distribution of α-olefins obtained satisfies the relation of obtaining a dimer in the largest amount, a trimer in a larger amount than that of a tetramer and a n-mer in a larger amount than that of a (n+1)-mer in an ordinary distribution according to a Shultz-Flory distribution.

At present, α-olefins are obtained according to the above Shultz-Flory distribution in many processes in which α-olefins are industrially produced. For example, a process in which α-olefins are produced by using a triethylaluminum catalyst is known, and it is known as well that involved therein are the problems that the α-olefins are obtained according to the Shultz-Flory distribution and that in addition thereto, the catalyst has to be used under the condition of a high temperature and a high pressure. However, α-olefins are different in a consumption amount and a price depending on carbon numbers thereof and heavily fluctuated in needs therefor. Accordingly, conventional processes in which α-olefins are produced according to the Shultz-Flory distribution have involved the problem that α-olefins having carbon atoms which are not less than those of particularly 1-octene have low yields. As a countermeasure for the above problem, the triethylaluminum catalyst is used to carry out a two-stage polymerization, whereby provided is the advantage that α-olefins having carbon atoms which are not less than those of 1-octene are obtained in large amounts according to a Poisson distribution. However, the defects of having to carry out the reaction under a high temperature and a high pressure using a large amount (stoichiometric amount) of the catalyst, indispensable recovering of the catalyst, complication of the apparatus and a reduction in a purity of the α-olefins produced have been involved therein. For example, processes in which 1-hexene and 1-octene are produced by using chromium compounds are disclosed in patent documents 1 to 4. However, it is reported therein that α-olefins obtained by the above processes comprise 1-hexene as a principal component and that a yield of 1-octene is low. On the other hand, transition metal compounds comprising aminophosphine as a ligand are disclosed in a patent document 5, but an object thereof is to produce polymers.

In light of the backgrounds described above, catalysts for enhancing the yields of α-olefins of 1-hexene up to 1-tetradecene each having 6 to 14 carbon atoms, particularly a yield of 1-octene are desired to be developed.

CITATION LIST

Patent Documents

Patent document 1: JP 6-329562-A
Patent document 2: JP 7-215896-A
Patent document 3: JP 8-183746-A
Patent document 4: JP 2002-532249-A
Patent document 5: JP 2003-261588-A

SUMMARY OF INVENTION

Technical Problem

The present invention has been made in light of the situation described above, and an object thereof is to provide a production process for α-olefin which does not comply the Shultz-Flory distribution and which is excellent in the yields of α-olefins of 1-hexene up to 1-tetradecene each having 6 to 14 carbon atoms, particularly a yield of 1-octene.

Intense researches repeated by the present inventors have resulted in finding the production conditions of the above production process by which the problems described above can be solved, and thus they have come to complete the present invention.

That is, the present invention relates to the following production process for α-olefin.

1. A production process for α-olefin characterized by polymerizing ethylene using (A) a chromium compound, (B) a ligand compound represented by the following Formula (1) and (C) a promoter:

(1)

wherein $L^1$ to $L^3$ each represent independently a substituted or non-substituted alicyclic hydrocarbon group having 5 to 30 carbon atoms, a substituted or non-substituted aromatic hydrocarbon group having 6 to 30 ring carbon atoms or a substituted or non-substituted aromatic heterocyclic group having 5 to 30 ring atoms.

2. The production process for α-olefin according to the item 1 described above, comprising the step of bringing the chromium compound (A) into contact with the ligand compound (B) and the step of reacting a reaction product thereof with the promoter (C).

3. The production process for α-olefin according to the item 1 or 2 described above, wherein the chromium compound (A) is represented by the following Formula (2):

$$CrX_nD_m \quad (2)$$

wherein X represents a σ-bonding ligand, and when a plurality of X is present, plural X may be the same or different; D represents a Lewis base, and when a plurality of D is present, plural D may be the same or different; n is an integer of 2 to 3 and represents a valence of Cr; and m represents an integer of 0 to 6.
4. The production process for α-olefin according to any of the items 1 to 3 described above, wherein $L^1$ to $L^3$ in Formula (1) each are independently a substituted or non-substituted phenyl group or a substituted or non-substituted cyclohexyl group, and a substituent thereof is an alkyl group having 1 to 4 carbon atoms, an alkoxy group having 1 to 4 carbon atoms or a cycloalkyl group having 5 to 6 ring carbon atoms.
5. The production process for α-olefin according to any of the items 1 to 4 described above, wherein the promoter (C) is aluminoxane.

Advantageous Effects of Invention

According to the present invention, provided is a production process for α-olefin which does not comply the Shultz-Flory distribution and which is excellent in the yields of α-olefins of 1-hexene up to 1-tetradecene each having 6 to 14 carbon atoms, particularly a yield of 1-octene.

DESCRIPTION OF EMBODIMENTS

The production process for α-olefin according to the present invention is characterized by polymerizing ethylene using the chromium compound (A), the ligand compound (B) represented by the following Formula (1) and the promoter (C):

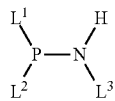   (1)

wherein $L^1$ to $L^3$ each represent independently a substituted or non-substituted alicyclic hydrocarbon group having 5 to 30 carbon atoms, a substituted or non-substituted aromatic hydrocarbon group having 6 to 30 ring carbon atoms or a substituted or non-substituted aromatic heterocyclic group having 5 to 30 ring atoms.

In the present specification, "a to b carbon atoms" in the expression of "a substituted or non-substituted X group having a to b carbon atoms" means the carbon atoms of the X group when it is non-substituted and does not include the carbon atoms of a substituent thereof when the X group is substituted.

Chromium Compound (A):

The chromium compound (A) used in the present invention shall not specifically be restricted as long as a chromium atom thereof can form a complex with the ligand compound (B) described later, and the compound represented by the following Formula (2) is preferably used:

$$CrX_nD_m \quad (2)$$

wherein X represents a σ-bonding ligand, and when a plurality of X is present, plural X may be the same or different; D represents a Lewis base, and when a plurality of D is present, plural D may be the same or different; n is an integer of 2 to 3 and represents a valence of Cr; and m represents an integer of 0 to 6, preferably 0 to 3.

X represents a σ-bonding ligand, and when a plurality of X is present, plural X may be the same or different and may be cross-linked with other X or D. The specific examples of the above σ-bonding ligand include a halogen atom, a hydrocarbon group having 1 to 20 carbon atoms, an alkoxy group having 1 to 20 carbon atoms, an aryloxy group having 6 to 20 carbon atoms, an amide group having 1 to 20 carbon atoms, a silicon-containing group having 1 to 20 carbon atoms, a phosphide group having 1 to 20 carbon atoms, a sulfide group having 1 to 20 carbon atoms, an acyl group having 1 to 20 carbon atoms, a substituted or non-substituted acetylacetonate, a substituted or non-substituted carboxylate and the like.

The halogen atom includes a chlorine atom, a fluorine atom, a bromine atom and an iodine atom.

The hydrocarbon group having 1 to 20 carbon atoms includes, to be specific, alkyl groups such as methyl, ethyl, propyl, butyl, hexyl, cyclohexyl, octyl and the like; alkenyl groups such as vinyl, propenyl, cyclohexenyl and the like; arylalkyl groups such as benzyl, phenylethyl, phenylpropyl and the like; and aryl groups such as phenyl, tolyl, dimethylphenyl, trimethylphenyl, ethylphenyl, propylphenyl, biphenyl, naphthyl, methylnaphthyl, anthracenyl, phenanthrenyl and the like. Among them, the alkyl groups such as methyl, ethyl, propyl and the like and the aryl groups such as phenyl and the like are preferred.

The alkoxy group having 1 to 20 carbon atoms includes alkoxy groups such as methoxy, ethoxy, propoxy, butoxy and the like. The aryloxy group having 6 to 20 carbon atoms includes phenoxy, methylphenoxy, dimethylphenoxy and the like.

The amide group having 1 to 20 carbon atoms includes alkylamide groups such as dimethylamide, diethylamide, dipropylamide, dibutylamide, dicyclohexylamide, methylethylamide and the like; alkenylamide groups such as divinylamide, dipropenylamide, dicyclohexenylamide and the like; arylalkylamide groups such as dibenzylamide, phenylethylamide, phenylpropylamide and the like; and arylamide groups such as diphenylamide, dinaphthylamide and the like.

The silicon-containing group having 1 to 20 carbon atoms includes mono-hydrocarbon-substituted silyl groups such as methylsilyl, phenylsilyl and the like; di-hydrocarbon-substituted silyl groups such as dimethylsilyl, diphenylsilyl and the like; tri-hydrocarbon-substituted silyl groups such as trimethylsilyl, triethylsilyl, tripropylsilyl, tricyclohexylsilyl, triphenylsilyl, dimethylphenylsilyl, methyldiphenylsilyl, tritolylsilyl, trinaphthylsilyl and the like; hydrocarbon-substituted silyl ether groups such as trimethylsilyl ether and the like; silicon-substituted alkyl groups such as trimethylsilylmethyl and the like; and silicon-substituted aryl groups such as trimethylsilylphenyl and the like. Among them, trimethylsilylmethyl, phenyldimethylsilylethyl and the like are preferred.

The phosphide group having 1 to 20 carbon atoms includes alkyl phosphide groups such as dimethyl phosphide, diethyl phosphide, dipropyl phosphide, dibutyl phosphide, dicyclohexyl phosphide, dioctyl phosphide and the like; alkenyl phosphide groups such as divinyl phosphide, dipropenyl phosphide, dicyclohexenyl phosphide and the like; arylalkyl phosphide groups such as dibenzyl phosphide, bis(phenylethylphenyl)phosphide and the like; and aryl phosphide groups such as diphenyl phosphide, ditolyl phosphide, dinaphthyl phosphide and the like.

The sulfide group having 1 to 20 carbon atoms includes alkyl sulfide groups such as methyl sulfide, ethyl sulfide, propyl sulfide, butyl sulfide, hexyl sulfide, cyclohexyl sulfide, octyl sulfide and the like; alkenyl sulfide groups such as vinyl sulfide, propenyl sulfide, cyclohexenyl sulfide and the like; arylalkyl sulfide groups such as benzyl sulfide, phenylethyl sulfide, phenylpropyl sulfide and the like; and aryl sulfide groups such as phenyl sulfide, tolyl sulfide, dimethylphenyl sulfide, trimethylphenyl sulfide, ethylphenyl sulfide, propylphenyl sulfide, biphenyl sulfide, naphthyl sulfide, methylnaphthyl sulfide, anthracenyl sulfide, phenanthrenyl sulfide and the like.

The acyl group having 1 to 20 carbon atoms includes alkylacyl groups such as formyl, acetyl, propionyl, butyryl, valeryl, palmitoyl, stearoyl, oleoyl and the like; arylacyl groups such as benzoyl, toluoyl, salicyloyl, cinnamoyl, naphthoyl, phthaloyl and the like; and oxalyl, malonyl, succinyl and the like which are derived respectively from dicarboxylic acids such as oxalic acid, malonic acid, succinic acid and the like.

On the other hand, D represents a Lewis base, and when a plurality of D is present, plural D may be the same or different and may be cross-linked with other D and X. The specific examples of the above Lewis base represented by D include amines, ethers, phosphines, thioethers and the like.

The amines include amines having 1 to 20 carbon atoms, and they include, to be specific, alkylamines such as methylamine, ethylamine, propylamine, butylamine, cyclohexylamine, methylethylamine, dimethylamine, diethylamine, dipropylamine, dibutylamine, dicyclohexylamine, methylethylamine and the like; alkenylamines such as vinylamine, propenylamine, cyclohexenylamine, divinylamine, dipropenylamine, dicyclohexenylamine and the like; arylalkylamines such as phenylamine, phenylethylamine, phenylpropylamine and the like; and arylamines such as diphenylamine, dinaphthylamine and the like.

The ethers include aliphatic homogeneous ether compounds such as methyl ether, ethyl ether, propyl ether, isopropyl ether, butyl ether, isobutyl ether, n-amyl ether, isoamyl ether and the like; aliphatic mixed ether compounds such as methyl ethyl ether, methyl propyl ether, methyl isopropyl ether, methyl n-amyl ether, methyl isoamyl ether, ethyl propyl ether, ethyl isopropyl ether, ethyl butyl ether, ethyl isobutyl ether, ethyl n-amyl ether, ethyl isoamyl ether and the like; aliphatic unsaturated ether compounds such as vinyl ether, allyl ether, methyl vinyl ether, methyl allyl ether, ethyl vinyl ether, ethyl allyl ether and the like; aromatic ether compounds such as anisole, phenetole, phenyl ether, benzyl ether, phenyl benzyl ether, α-naphthyl ether, β-naphthyl ether and the like; and cyclic ether compounds such as ethylene oxide, propylene oxide, trimethylene oxide, tetrahydrofuran, tetrahydropyran, dioxane and the like.

The phosphines include phosphines having 1 to 20 carbon atoms, and they include, to be specific, alkylphosphines including mono-hydrocarbon-substituted phosphines such as methylphosphine, ethylphosphine, propylphosphine, butylphosphine, hexylphosphine, cyclohexylphosphine, octylphosphine and the like; di-hydrocarbon-substituted phosphines such as dimethylphosphine, diethylphosphine, dipropylphosphine, dibutylphosphine, dihexylphosphine, dicyclohexylphosphine, dioctylphosphine and the like; and tri-hydrocarbon-substituted phosphines such as trimethylphosphine, triethylphosphine, tripropylphosphine, tributylphosphine, trihexylphosphine, tricyclohexylphosphine, trioctylphosphine and the like; monoalkenylphosphines such as vinylphosphine, propenylphosphine, cyclohexenylphosphine and the like and dialkenylphosphines obtained by substituting hydrogen atoms of phosphines with two alkenyls; trialkenylphosphines obtained by substituting hydrogen atoms of phosphines with three alkenyls; and arylphosphines including arylalkylphosphines such as benzylphosphine, phenylethylphosphine, phenylpropylphosphine and the like; diarylalkylphosphines or aryldialkylphosphines obtained by substituting hydrogen atoms of phosphines with three aryls or alkenyls; phenylphosphine, tolylphosphine, dimethylphenylphosphine, trimethylphenylphosphine, ethylphenylphosphine, propylphenylphosphine, biphenylphosphine, naphthylphosphine, methylnaphthylphosphine, anthracenylphosphine, phenanthrenylphosphine; di(alkylaryl)phosphines obtained by substituting hydrogen atoms of phosphines with two alkylaryls; and tri(alkylaryl)phosphines obtained by substituting hydrogen atoms of phosphines with three alkylaryls. The thioethers include the sulfides described above.

The specific examples of the chromium compound (A) described above include chromium (III) tris(acetylacetonate), chromium (III) tris(ethylhexanate), tri-t-butoxychromium (III), chromium trichloride, chromium tribromide, chromium dichloride, trichlorotris (THF) chromium and the like, and chromium (III) tris(acetylacetonate), chromium trichloride, chromium dichloride, trichlorotris (THF) chromium, dichlorobis (THF) chromium and the like are preferably used.

Ligand Compound (B):

The ligand compound (B) used in the present invention is represented by the following Formula (1):

(1)

wherein $L^1$ to $L^3$ each represent independently a substituted or non-substituted alicyclic hydrocarbon group having 5 to 30 carbon atoms, a substituted or non-substituted aromatic hydrocarbon group having 6 to 30 ring carbon atoms or a substituted or non-substituted aromatic heterocyclic group having 5 to 30 ring atoms.

$L^1$ to $L^3$ described above are preferably a substituted or non-substituted alicyclic hydrocarbon group having 5 to 14 carbon atoms or a substituted or non-substituted aromatic hydrocarbon group having 6 to 14 ring carbon atoms.

The specific examples of the alicyclic hydrocarbon group represented by $L^1$ to $L^3$ described above include cyclopentyl, cyclohexyl, cyclooctyl and the like, and it is preferably cyclopentyl or cyclohexyl.

The examples of the aromatic hydrocarbon group represented by $L^1$ to $L^3$ described above include phenyl, naphthyl, phenanthryl, biphenylyl, terphenylyl, quaterphenylyl, fluoranthenyl, triphenylenyl, fluorenyl, benzo[c]phenanthrenyl, benzo[a]triphenylenyl, naphtho[1,2-c]phenanthrenyl, naphtho[1,2-a]triphenylenyl, dibenzo[a,c]triphenylenyl, benzo[b]fluoranthenyl and the like, and it is preferably phenyl, 4-biphenylyl, 3-biphenylyl, 5'-m-terphenylyl, 1-naphthyl, fluorene-2-yl, 2-naphthyl and 9-phenanthrenyl.

The examples of the substituted aromatic hydrocarbon group represented by $L^1$ to $L^3$ include 2-methylphenyl, 3-methylphenyl, 4-methylphenyl, 2-ethylphenyl, 3-ethylphenyl, 4-ethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-4-methoxyphenyl, 2-methyl-6-methoxyphenyl, 2,4,5-trimethylphenyl, 2,4,6-trimethylphenyl, 4-n-butylphenyl, 4-t-butylphenyl and the like.

The aromatic heterocyclic group represented by $L^1$ to $L^3$ described above is preferably groups containing at least one hetero atom selected from a nitrogen atom, an oxygen atom and a sulfur atom, and the specific examples thereof include pyrrolyl, furyl, thienyl, pyridyl, pyridazinyl, pyrimidinyl, pyrazinyl, triazinyl, imidazolyl, oxazolyl, thiazolyl, pyrazolyl, isoxazolyl, isothiazolyl, oxadiazolyl, thiadiazolyl, triazolyl, indolyl, isoindolyl, benzofuranyl, isobenzofuranyl, benzothiophenyl, indolizinyl, quinolizinyl, quinolyl, isoquinolyl, cinnolyl, phthalazinyl, quinazolinyl, quinoxalinyl, benzimidazolyl, benzoxazolyl, benzothiazolyl, indazolyl, benzisoxazolyl, benzisothiazolyl, carbazolyl, dibenzofuranyl, dibenzothiophenyl, phenanthridinyl, acridinyl, phenanthrolinyl, phenazinyl, phenothiazinyl, phenoxazinyl and xanthenyl, and they are preferably furyl, thienyl, benzofuranyl, benzothiophenyl, dibenzofuranyl and dibenzothiophenyl.

$L^1$ to $L^3$ described above each are preferably independently a substituted or non-substituted aromatic hydrocarbon group having 6 to 30 ring carbon atoms or a substituted or non-substituted aromatic heterocyclic group having 5 to 30 ring atoms, more preferably a substituted or non-substituted aromatic hydrocarbon group having 6 to 30 ring carbon atoms and particularly preferably a substituted or non-substituted phenyl group.

The substituted phenyl group used as $L^1$ to $L^3$ described above is particularly preferably the phenyl group having an alkyl group having 1 to 20 carbon atoms or an alkoxy group having 1 to 20 carbon atoms as a substituent.

Optional substituents referred to as "substituted or non-substituted" described above and described later include a halogen atom, a cyano group, an alkyl group having 1 to 20 (preferably 1 to 5) carbon atoms, a cycloalkyl group having 3 to 20 (preferably 5 to 12) carbon atoms, an alkoxy group having 1 to 20 (preferably 1 to 5) carbon atoms, a haloalkyl group having 1 to 20 (preferably 1 to 5) carbon atoms, a haloalkoxy group having 1 to 20 (preferably 1 to 5) carbon atoms, an alkylsilyl group having 1 to 10 (preferably 1 to 5) carbon atoms, an aryl group having 6 to 30 (preferably 6 to 18) ring carbon atoms, an aryloxy group having 6 to 30 (preferably 6 to 18) ring carbon atoms, an arylsilyl group having 6 to 30 (preferably 6 to 18) carbon atoms, an aralkyl group having 7 to 30 (preferably 7 to 20) carbon atoms and a heteroaryl group having 5 to 30 (preferably 5 to 18) ring atoms.

A use ratio of the component (A) and the component (B) falls in a range of preferably 0.1 to 10, more preferably 0.2 to 5 and particularly preferably 0.5 to 3.0 in terms of a mole ratio of the component (B)/the component (A).

Also, one kind or two or more kinds of the component (B) can be used.

Promoter (C):

The specific examples of the promoter (C) used in the present invention include (C-1) aluminoxane and (C-2) a boron compound.

(C-1) Aluminoxane:

Capable of being listed as the aluminoxane of the component (C-1) are chain aluminoxane represented by Formula (I):

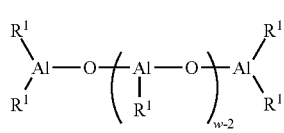

(I)

wherein $R^1$ represents a hydrocarbon group such as an alkyl group having 1 to 20 carbon atoms, preferably 1 to 12 carbon atoms, an alkenyl, group, an aryl group, an arylalkyl group and the like or a halogen atom; w represents an average polymerization degree and is an integer of usually 2 to 50, preferably 2 to 40; and respective $R^1$ may be the same or different; and cyclic aluminoxane represented by Formula (II):

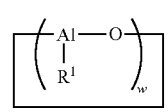

(II)

wherein $R^1$ and w are the same as those shown in Formula (I).

The specific examples of the aluminoxane (C-1) include methylaluminoxane (MAO), methylisobutylaluminoxane (MMAO), ethylaluminoxane (EMAO), isobutylaluminoxane (IBAO) and the like, and methylaluminoxane (MAO) or methylisobutylaluminoxane (MMAO) is preferably used.

A production process for the aluminoxane described above includes a process in which alkylaluminum is brought into contact with a condensing agent such as water and the like, but means thereof shall not specifically be restricted, and the reaction can be carried out according a publicly known method.

Available are, for example, (1) a process in which an organic aluminum compound is dissolved in an organic solvent and in which the solution obtained is brought into contact with water, (2) a process in which an organic aluminum compound is added in the beginning in polymerization and in which water is added later on, (3) a process in which crystal water contained in metal salts and the like and water adsorbed onto inorganic matters and organic matters are reacted with organic aluminum compounds and (4) a process in which tetraalkyldialuminoxane is reacted with trialkylaluminum and in which water is further reacted therewith. Incidentally, the aluminoxane may be insoluble in toluene. The above aluminoxanes may be used alone or in combination of two or more kinds thereof.

A use ratio of the component (A) and the component (C) falls in a range of preferably 1 to 10,000, more preferably 10 to 1,000 in terms of a mole ratio of the component (C)/the component (A). One kind or two or more kinds selected from the component (C-1) and the component (C-2) can be used as the component (C).

(C-2) Boron Compound:

Tris(pentafluorophenyl)boron, dimethylanilinium tetrakis(pentafluorophenyl)borate, dimethylanilinium borate, trityl tetrakis(pentafluorophenyl)borate and the like can be listed as the specific examples of the boron compound (C-2).

(D) Organic Aluminum Compound:

Further, in the production process for α-olefin according to the present invention, the organic aluminum compound can be used as the component (D) in addition to the components (A) to (C) described above. In this regard, a compound represented by Formula (III):

$$R^2_v AlJ_{3-v}$$  (III)

wherein $R^2$ represents an alkyl group having 1 to 10 carbon atoms; J represents a hydrogen atom, an alkoxy group having 1 to 20 carbon atoms, an aryl group having 6 to 20 carbon atoms or a halogen atom; and v is an integer of 1 to 3, is used as the organic aluminum compound of the component (D).

The specific examples of the compound represented by Formula (III) described above include trimethylaluminum, triethylaluminum, triisopropylaluminum, triisobutylaluminum, dimethylaluminum chloride, diethylaluminum chloride, methylaluminum dichloride, ethylaluminum dichloride, dimethylaluminum fluoride, diisobutylaluminum hydride, diethylaluminum hydride, ethylaluminum sesquichloride and the like. Among them, the organic aluminum compounds to which a hydrocarbon group having 4 or more carbon atoms is bonded are preferred from the viewpoint that they are excellent in a high temperature stability, and the organic aluminum compounds to which a hydrocarbon group having 4 to 8 carbon atoms is bonded are more preferred from the above viewpoint. When the reaction temperature is 100° C. or higher, the organic aluminum compounds to which a hydrocarbon group having 6 to 8 carbon atoms is bonded are further more preferred. The organic aluminum compounds (D) described above may be used alone or in combination of two or more kinds thereof.

A use ratio of the component (A) and the component (D) falls in a range of preferably 1:1 to 1:10,000, more preferably 1:5 to 1:2,000 and further preferably 1:10 to 1:1,000 in terms of a mole ratio. Use of the above component (D) makes it possible to enhance the polymerization activity per chromium, but if it is added too much, the organic aluminum compound (D) is not used efficiently, and a lot of a load is applied on an after-treating step. Accordingly, it is not preferred.

In the production process for α-olefin according to the present invention, ethylene is polymerized under the presence of the components (A) to (C) described above. Any two or more kinds of the components (A) to (C) may be brought into contact in advance and then added to the polymerization solvent, or the components (A) to (C) can be mixed as well at the same time. The mixing order thereof shall not be restricted, and the component (A) is preferably brought into contact in advance with the component (B).

The polymerization temperature is preferably 0 to 150° C., more preferably 20 to 80° C.

The polymerization pressure is preferably an atmospheric pressure to 10 MPa, more preferably 0.2 to 8.0 MPa and particularly preferably 0.5 to 5.0 MPa.

The polymerization solvent includes benzene, toluene, xylene, pentane, heptane, cyclohexane, methylcyclohexane and the like, and toluene and cyclohexane are preferably used.

In the production process for α-olefin according to the present invention, a ratio of 1-octene in the α-olefins obtained is preferably not lower than a ratio of 1-hexene. Also, a ratio of 1-octene is preferably 10% by mass or more, more preferably 15% by mass or more, further preferably 20% by mass or more and particularly preferably 25% by mass or more.

EXAMPLES

Next, the present invention shall be explained in further details with reference to examples, but the present invention shall by no means be restricted by these examples. The measuring methods of the physical properties and the measuring equipments shall be shown below.

Mass Ratios of the Respective α-Olefins:

A fixed amount of undecane (C11) was added as an internal standard solution to the reaction liquid, and the solution was measured by a gas chromatography (GC) on the following conditions to determine the mass ratios of the respective α-olefin components (C4 to C18) based on the internal standard solution C11.

GC Measuring Conditions:
Column: Ultra 2 (25 m×0.2 mm×0.33 μm)
Injection inlet temperature: 270° C.
Detector temperature: 270° C.
Column temperature: 40 to 200° C. (1.5° C./minute), 200 to 270° C. (8° C./minute)

Example 1

Preparation of Chromium Complex Solution

A 50 ml Shlenk flask equipped with a stirrer which was substituted with nitrogen was charged with 20 ml (40 μmol) of a chromium tris(acetylacetonate) toluene solution and 6 ml (120 μmol) of a solution of a ligand compound A represented by the following formula, and the mixture was stirred at room temperature for about 2 hours to prepare a chromium complex solution. The solution was a pale purple homogeneous solution.

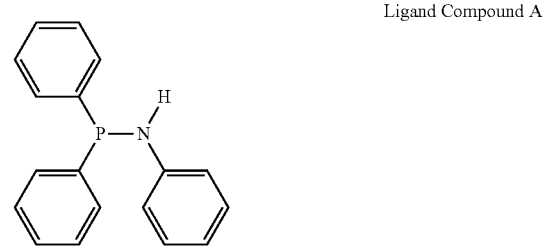 [SMILES: c1ccc(NP(c2ccccc2)c2ccccc2)cc1]

Ligand Compound A

Polymerization:

An autoclave of 1 L equipped with a stirrer which was sufficiently dehydrated and substituted with nitrogen was charged with 300 ml of a dried solvent toluene and then 17.88 ml (27.5 μmol) of the chromium complex solution described above and 2.75 ml (8250 μmol) of a toluene solution of methylaluminoxane to start stirring the mixture. The reaction temperature was elevated up to 40° C., and when the temperature reached 40° C., the flask was charged with ethylene at 4 MPa to start the reaction. After carrying out the reaction for 1 hour, 30 ml of ethanol was added thereto under applied pressure to deactivate the catalyst. After the reaction liquid was cooled down to room temperature, the pressure was removed, and the autoclave was opened. Undecane 3.5 g which was an internal standard solution for GC analysis was added to the reaction liquid, and the mixture was stirred well. The reaction liquid was analyzed by GC to determine a distribution and a purity of the respective α-olefins. When a polymer was by-produced, the reaction liquid was filtrated under reduced pressure, and the residue was dried in air for a day, followed by measuring a weight thereof. The results thereof are shown in Table 1.

Example 2

Preparation of a chromium complex solution and polymerization of ethylene were carried out in the same manners as in Example 1, except that a use amount of the ligand compound A solution was changed from 6 ml (120 μmol) to 2 ml (40 μmol). The results thereof are shown in Table 1.

Example 3

A n-BuLi hexane solution (2.05 mmol, 0.82 mL) was added to a THF (15 mL) solution of the ligand compound A (0.54 g, 1.96 mmol) at −10° C. The reaction mixture was stirred at room temperature through a night, and the solution thus obtained was added to a THF (5 mL) suspension of $CrCl_2(THF)_2$ (0.27 g, 1.01 mmol). After stirring the mixture for 18 hours, the solvent was removed by distillation under reduced pressure, and the solid residue was redissolved in toluene. A small amount of a colorless insoluble matter was separated by filtration, and the solvent was removed from the resulting brown solution by distillation under reduced pressure. A greenish brown solid matter thus obtained was used as a catalyst to polymerize ethylene in the same manner as in Example 1. The results thereof are shown in Table 1.

Example 4

Ethylene was polymerized in the same manner as in Example 2, except that the solvent was changed from toluene to cyclohexane. The results thereof are shown in Table 1.

Example 5

Ethylene was polymerized in the same manner as in Example 1, except that a solution of the following ligand compound B was used in place of the ligand compound A solution. The results thereof are shown in Table 1.

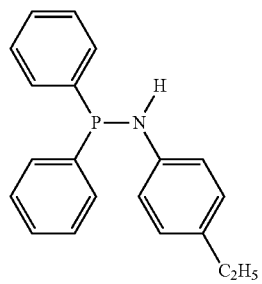

Ligand Compound B

Example 6

Ethylene was polymerized in the same manner as in Example 1, except that a solution of the following ligand compound C was used in place of the ligand compound A solution. The results thereof are shown in Table 1.

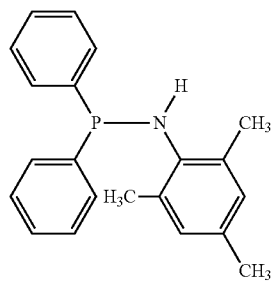

Ligand Compound C

Example 7

Ethylene was polymerized in the same manner as in Example 1, except that a solution of the following ligand compound D was used in place of the ligand compound A solution. The results thereof are shown in Table 1.

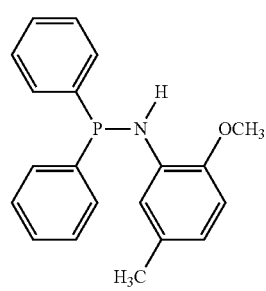

Ligand Compound C

Example 8

Preparation of a chromium complex solution and polymerization of ethylene were carried out in the same manners as in Example 7, except that a use amount of the ligand compound D solution was changed from 6 ml (120 μmol) to 2 ml (40 μmol). The results thereof are shown in Table 1.

Comparative Example 1

Ethylene was polymerized in the same manner as in Example 1, except that a solution of the following ligand compound X was used in place of the ligand compound A solution. The results thereof are shown in Table 1.

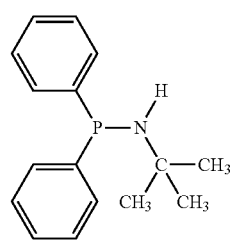

Ligand Compound X

Comparative Example 2

Ethylene was polymerized in the same manner as in Example 1, except that the ligand compound A solution was not added. The results thereof are shown in Table 1.

TABLE 1

|  |  | Example | | | | | | | | Comparative Example | |
|---|---|---|---|---|---|---|---|---|---|---|---|
|  |  | 1 | 2 | 3 | 4 | 5 | 6 | 7 | 8 | 1 | 2 |
| Chromium compound (A) | Kind | $Cr(acac)_3$ | $Cr(acac)_3$ | $CrCl_2(THF)_2$ | $Cr(acac)_3$ | $Cr(acac)_3$ | $Cr(acac)_3$ | $Cr(acac)_3$ | $Cr(acac)_3$ | $Cr(acac)_3$ | $Cr(acac)_3$ |
|  | (μmol) | 27.5 | 27.5 | 27.5 | 27.5 | 27.5 | 27.5 | 27.5 | 27.5 | 27.5 | 27.5 |
| Ligand compound (B) | Kind | A | A | A | A | B | C | D | D | X | — |
|  | (μmol) | 82.5 | 27.5 | 13.75 | 27.5 | 82.5 | 82.5 | 82.5 | 27.5 | 82.5 | — |

TABLE 1-continued

|  |  | Example | | | | | | | | Comparative Example | |
|---|---|---|---|---|---|---|---|---|---|---|---|
|  |  | 1 | 2 | 3 | 4 | 5 | 6 | 7 | 8 | 1 | 2 |
| (B)/(A) ratio | (mole ratio) | 3 | 1 | 0.5 | 1 | 3 | 3 | 3 | 1 | 3 | — |
| (C) MAO | (mM) | 8.25 | 8.25 | 8.25 | 8.25 | 8.25 | 8.25 | 8.25 | 8.25 | 8.25 | 8.25 |
| Al/Cr ratio | (mole ratio) | 300 | 300 | 300 | 300 | 300 | 300 | 300 | 300 | 300 | 300 |
| Reaction temperature | (° C.) | 45 to 55 | 45 to 55 | 45 to 55 | 45 to 55 | 40 to 45 | 40 to 45 | 40 to 45 | 40 to 45 | 45 to 55 | 45 to 55 |
| Reaction pressure | (MPa) | 4 | 4 | 4 | 4 | 4 | 4 | 4 | 4 | 4 | 4 |
| Kind of solvent |  | Toluene | Toluene | Toluene | Cyclohexane | Toluene | Toluene | Toluene | Toluene | Toluene | Toluene |
| Activity | (g/mM · Cr) | 890 | 1340 | 2420 | 1800 | 900 | 600 | 110 | 1100 | 1790 | 520 |
| Product distribution |  |  |  |  |  |  |  |  |  |  |  |
| C4 | (mass %) | 1.6 | 11.8 | 14.4 | 2.0 | 5.4 | 13.7 | 3.1 | 8.6 | 12.8 | 12.9 |
| C6 | (mass %) | 11.9 | 25.3 | 25.3 | 10.2 | 23.5 | 27.0 | 13.3 | 20.6 | 25.2 | 28.0 |
| C8 | (mass %) | 72.4 | 32.4 | 29.5 | 69.8 | 33.7 | 29.3 | 59.3 | 40.1 | 23.7 | 25.3 |
| C10 | (mass %) | 4.3 | 11.9 | 14.0 | 4.6 | 15.0 | 13.2 | 7.2 | 11.5 | 15.1 | 13.6 |
| C12 | (mass %) | 3.0 | 7.7 | 7.8 | 4.6 | 9.6 | 7.8 | 5.2 | 7.5 | 9.8 | 8.6 |
| C14 | (mass %) | 2.8 | 5.2 | 4.6 | 3.5 | 6.0 | 4.6 | 4.3 | 4.5 | 6.6 | 5.5 |
| C16 | (mass %) | 2.4 | 3.5 | 2.7 | 3.2 | 4.1 | 2.8 | 3.9 | 4.5 | 4.1 | 3.5 |
| C18 | (mass %) | 1.7 | 2.2 | 1.7 | 2.2 | 2.8 | 1.7 | 3.5 | 2.8 | 2.6 | 2.4 |

In the production process of Comparative Examples 1 and 2, a yield of 1-octene (C8) is lower than a yield of 1-hexene (C6). In contrast with this, a composition distribution of the α-olefins obtained by the production process of the present invention does not comply the Shultz-Flory distribution and is characterized, to be specific, by that a yield of 1-octene (C8) is higher than a yield of 1-hexene (C6), and it can be confirmed that they are excellent in a yield of 1-octene.

In Table 1, a yield of 1-butene (C4) is low in all of Examples 1 to 8 and Comparative Examples 1 to 2, and this trend is understood to be attributable to that 1-butene (C4) is light and therefore volatilized.

INDUSTRIAL APPLICABILITY

The α-olefins obtained by the production process of the present invention are useful for applications of comonomers of LLDPE, synthetic lubricants, surfactants and the like.

The invention claimed is:

1. A process for producing an α-olefin, the process comprising polymerizing ethylene in the presence of (A) a chromium compound, (B) a ligand compound represented by Formula (1) and (C) a promoter:

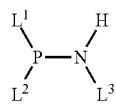
(1)

wherein $L^1$ to $L^3$ each represent independently a substituted or non-substituted alicyclic hydrocarbon group having 5 to 30 carbon atoms, a substituted or non-substituted aromatic hydrocarbon group having 6 to 30 ring carbon atoms or a substituted or non-substituted aromatic heterocyclic group having 5 to 30 ring atoms.

2. The process of claim 1, comprising contacting the chromium compound (A) with the ligand compound (B) to form a reaction product, and reacting the reaction product with the promoter (C).

3. The process of claim 1, wherein the chromium compound (A) is represented by Formula (2):

$$CrX_nD_m \qquad (2)$$

wherein X represents a σ-bonding ligand, and when a plurality of X is present, plural X may be identical or different; D represents a Lewis base, and when a plurality of D is present, plural D may be identical or different; n is an integer of 2 to 3 and represents a valence of Cr; and m represents an integer of 0 to 6.

4. The process of claim 1, wherein $L^1$ to $L^3$ in Formula (1) each are independently a substituted or non-substituted phenyl group or a substituted or non-substituted cyclohexyl group, and a substituent thereof is an alkyl group having 1 to 4 carbon atoms, an alkoxy group having 1 to 4 carbon atoms or a cycloalkyl group having 5 to 6 ring carbon atoms.

5. The process of claim 1, wherein the promoter (C) is aluminoxane.

6. The process of claim 1, wherein at least one of $L^1$ to $L^3$ in Formula (1) is a substituted or non-substituted alicyclic hydrocarbon group having 5 to 30 carbon atoms.

7. The process of claim 1, wherein at least one of $L^1$ to $L^3$ in Formula (1) is a substituted or non-substituted aromatic hydrocarbon group having 6 to 30 ring carbon atoms.

8. The process of claim 1, wherein at least one of $L^1$ to $L^3$ in Formula (1) is a substituted or non-substituted aromatic heterocyclic group having 5 to 30 ring atoms.

9. The process of claim 4, wherein $L^1$ to $L^3$ in Formula (1) each are independently a substituted or non-substituted phenyl group.

10. The process of claim 4, wherein $L^1$ to $L^3$ in Formula (1) each are independently a substituted or non-substituted cyclohexyl group.

11. The process of claim 2, wherein the chromium compound (A) is represented by Formula (2):

$$CrX_nD_m \qquad (2)$$

wherein X represents a σ-bonding ligand, and when a plurality of X is present, plural X may be identical or different; D represents a Lewis base, and when a plurality of D is present, plural D may be identical or different; n is an integer of 2 to 3 and represents a valence of Cr; and m represents an integer of 0 to 6.

12. The process of claim 2, wherein $L^1$ to $L^3$ in Formula (1) each are independently a substituted or non-substituted phenyl group or a substituted or non-substituted cyclohexyl group, and a substituent thereof is an alkyl group having 1 to 4 carbon atoms, an alkoxy group having 1 to 4 carbon atoms or a cycloalkyl group having 5 to 6 ring carbon atoms.

13. The process of claim 3, wherein $L^1$ to $L^3$ in Formula (1) each are independently a substituted or non-substituted phenyl group or a substituted or non-substituted cyclohexyl group, and a substituent thereof is an alkyl group having 1 to 4 carbon atoms, an alkoxy group having 1 to 4 carbon atoms or a cycloalkyl group having 5 to 6 ring carbon atoms.

14. The process of claim 11, wherein $L^1$ to $L^3$ in Formula (1) each are independently a substituted or non-substituted phenyl group or a substituted or non-substituted cyclohexyl group, and a substituent thereof is an alkyl group having 1 to 4 carbon atoms, an alkoxy group having 1 to 4 carbon atoms or a cycloalkyl group having 5 to 6 ring carbon atoms.

\* \* \* \* \*